(12) United States Patent
Brand

(10) Patent No.: US 7,981,124 B2
(45) Date of Patent: Jul. 19, 2011

(54) MEDICAL DEVICE FOR APPLYING PURSE STRING SUTURES

(75) Inventor: Marc I. Brand, Deerfield, IL (US)

(73) Assignee: Misder, LLC, Niwot, CO (US)

( * ) Notice: Subject to any disclaimer, the term of this patent is extended or adjusted under 35 U.S.C. 154(b) by 1140 days.

(21) Appl. No.: 11/696,677

(22) Filed: Apr. 4, 2007

(65) Prior Publication Data
US 2008/0249544 A1 Oct. 9, 2008

(51) Int. Cl.
*A61B 17/04* (2006.01)

(52) U.S. Cl. ........................................... 606/144

(58) Field of Classification Search .................. 606/139, 606/144–150, 232; 112/69, 169, 171, 470.26; 623/2.11
See application file for complete search history.

(56) References Cited

U.S. PATENT DOCUMENTS

| | | | | |
|---|---|---|---|---|
| 4,198,982 A | * | 4/1980 | Fortner et al. | 227/179.1 |
| 4,304,236 A | * | 12/1981 | Conta et al. | 227/179.1 |
| 4,345,600 A | * | 8/1982 | Rothfuss | 606/148 |
| 4,592,354 A | * | 6/1986 | Rothfuss | 227/179.1 |
| 4,602,635 A | | 7/1986 | Mulhollan et al. | |
| 4,667,673 A | * | 5/1987 | Li | 606/153 |
| 4,749,114 A | | 6/1988 | Green | |
| 4,773,420 A | * | 9/1988 | Green | 227/178.1 |
| 4,821,939 A | | 4/1989 | Green | |
| 4,841,888 A | | 6/1989 | Mills et al. | |
| 4,915,107 A | | 4/1990 | Rebuffat et al. | |
| 4,917,114 A | * | 4/1990 | Green et al. | 227/179.1 |
| 4,930,674 A | * | 6/1990 | Barak | 227/179.1 |
| 5,037,021 A | | 8/1991 | Mills et al. | |
| D322,478 S | * | 12/1991 | Green et al. | D24/145 |
| 5,080,663 A | | 1/1992 | Mills et al. | |
| 5,122,156 A | * | 6/1992 | Granger et al. | 606/219 |
| 5,188,636 A | | 2/1993 | Fedotov | |
| 5,205,459 A | * | 4/1993 | Brinkerhoff et al. | 227/179.1 |
| 5,222,963 A | * | 6/1993 | Brinkerhoff et al. | 606/153 |
| 5,242,457 A | | 9/1993 | Akopov et al. | |
| 5,271,544 A | * | 12/1993 | Fox et al. | 227/180.1 |
| 5,282,810 A | * | 2/1994 | Allen et al. | 606/150 |
| 5,285,944 A | * | 2/1994 | Green et al. | 227/179.1 |
| 5,411,508 A | * | 5/1995 | Bessler et al. | 606/153 |
| 5,425,737 A | | 6/1995 | Burbank et al. | |
| 5,484,451 A | | 1/1996 | Akopov et al. | |

(Continued)

OTHER PUBLICATIONS

International Search Report issued by the U.S. Patent Office in PCT/US08/58991.

*Primary Examiner* — Darwin P Erezo
*Assistant Examiner* — Son Dang
(74) *Attorney, Agent, or Firm* — McDonnell Boehnen Hulbert & Berghoff LLP

(57) ABSTRACT

A surgical instrument for applying purse string sutures to tissue is provided that includes two circular discs that each have notches within a perimeter of the disc for receiving tissue and through which a suture wire may pass. The device also includes push plates for advancing the suture wires through the notches of the two circular discs and into portions of the tissue. Suture is placed within each push plate and is connected to ends of the suture wires. Suction is applied to the circular discs through a shaft to draw the tissue into the respective notches of the circular discs so that the suture wires may be advanced through the tissue and the sutures can then be pulled through the tissue to create two purse-string sutures.

20 Claims, 5 Drawing Sheets

U.S. PATENT DOCUMENTS

| | | | |
|---|---|---|---|
| 5,490,856 A * | 2/1996 | Person et al. | 606/139 |
| 5,496,332 A * | 3/1996 | Sierra et al. | 606/139 |
| 5,549,122 A * | 8/1996 | Detweilwer | 128/898 |
| 5,722,981 A | 3/1998 | Stevens | 606/148 |
| 5,814,054 A * | 9/1998 | Kortenbach et al. | 606/139 |
| 5,860,990 A * | 1/1999 | Nobles et al. | 606/144 |
| 5,891,159 A | 4/1999 | Sherman et al. | |
| 5,915,616 A * | 6/1999 | Viola et al. | 227/179.1 |
| 5,951,590 A * | 9/1999 | Goldfarb | 606/232 |
| 6,083,241 A * | 7/2000 | Longo et al. | 606/219 |
| 6,126,058 A * | 10/2000 | Adams et al. | 227/180.1 |
| 6,193,129 B1 * | 2/2001 | Bittner et al. | 227/180.1 |
| 6,245,079 B1 * | 6/2001 | Nobles et al. | 606/144 |
| 6,517,556 B1 * | 2/2003 | Monassevitch | 606/151 |
| 6,860,895 B1 * | 3/2005 | Akerfeldt et al. | 606/215 |
| 6,959,851 B2 * | 11/2005 | Heinrich | 227/175.1 |
| 6,997,931 B2 | 2/2006 | Sauer et al. | |
| 7,083,629 B2 | 8/2006 | Weller et al. | |
| 7,303,106 B2 * | 12/2007 | Milliman et al. | 227/175.1 |
| 2003/0183671 A1 * | 10/2003 | Mooradian et al. | 227/175.1 |
| 2005/0043746 A1 * | 2/2005 | Pollak et al. | 606/144 |
| 2005/0070922 A1 | 3/2005 | Field et al. | |
| 2005/0228414 A1 | 10/2005 | Mayoral | |
| 2006/0000869 A1 * | 1/2006 | Fontayne | 227/175.1 |
| 2006/0020167 A1 | 1/2006 | Sitzmann | |
| 2007/0179509 A1 * | 8/2007 | Nagata et al. | 606/144 |
| 2007/0293876 A1 * | 12/2007 | Abe et al. | 606/144 |

* cited by examiner

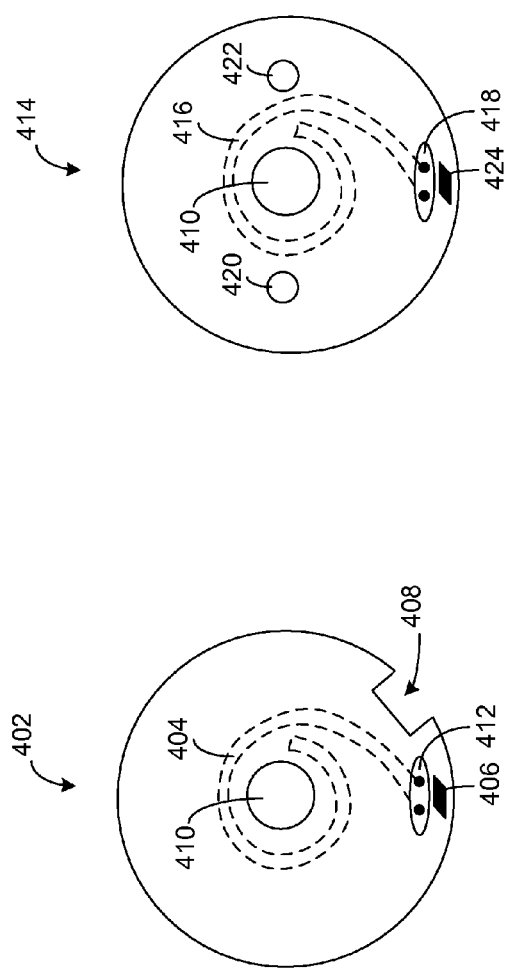
FIGURE 4B
FIGURE 4A
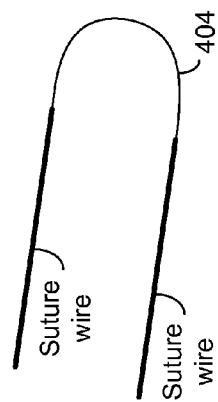
Each suture wire is connected to one end of the suture
FIGURE 5

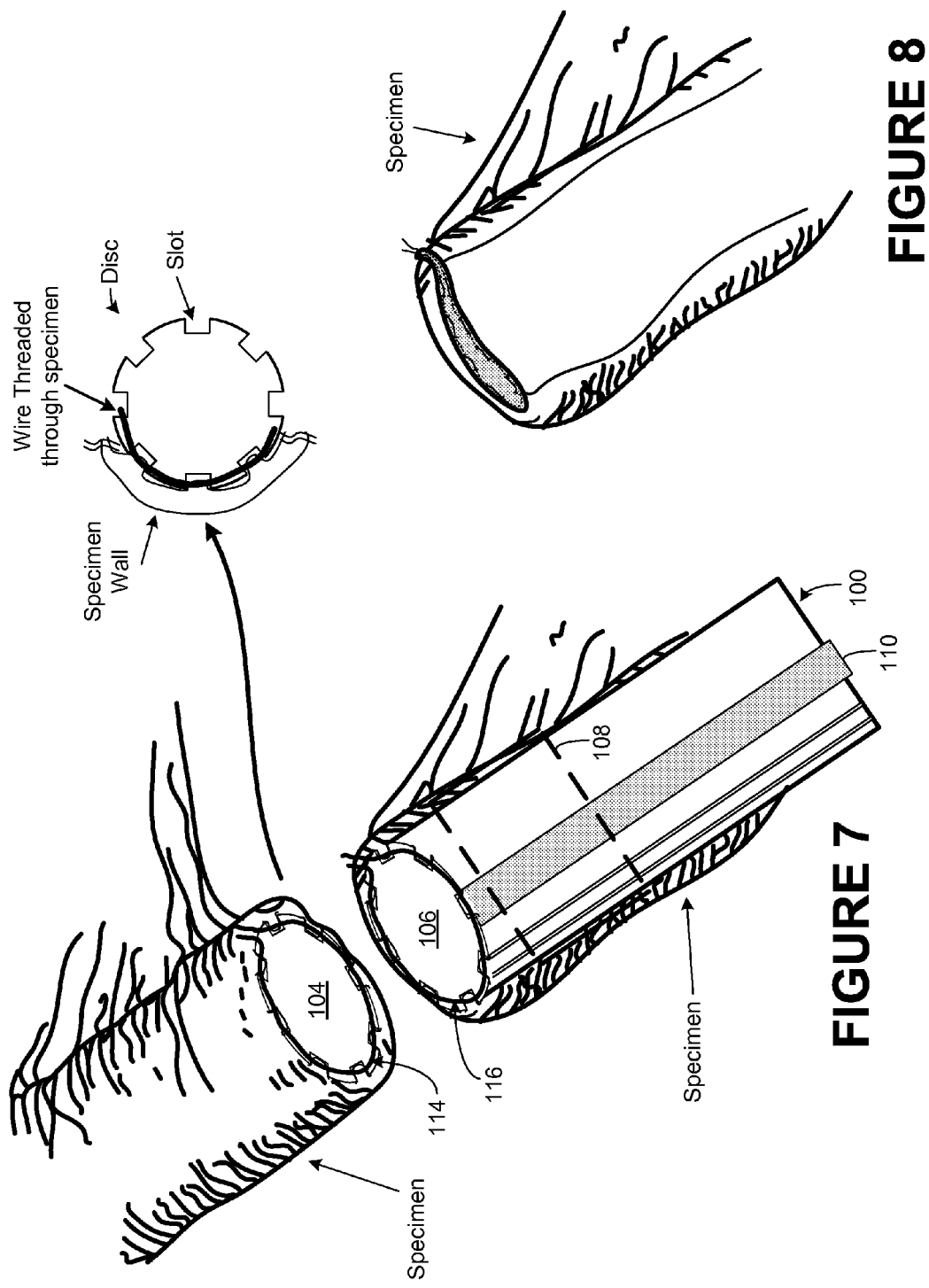

MEDICAL DEVICE FOR APPLYING PURSE STRING SUTURES

FIELD

The present application generally relates to a surgical instrument for applying purse string sutures to human tissue and, more particularly, to a surgical instrument and method in which multiple purse string sutures are secured to human tissue from within a vessel so as to close an end of a tubular vessel. The surgical instrument of the present application may be used to apply purse-string sutures prior to an end-to-end anastomosis procedure during laparoscopic or open abdominal surgery to remove portions of the colon, for example.

BACKGROUND

Many medical procedures today require the need to reconnect internal vessels after a portion has been removed. For example, in various procedures such as where a section of colon has been excised, it is necessary to rejoin the remaining portions of the colon through an end-to-end anastomosis (e.g., connection of healthy sections of the colon or rectum after a cancerous or otherwise diseased portion has been surgically removed). Many medical devices are available to perform the reconnection of the two portions of the colon using a device to apply a double row of staples, for example. Other existing known devices to perform an anastomosis on the colon, for example, require a surgeon to dissect the diseased portion of the colon, secure the separable ends of an anastomosis device into the healthy portions of the colon with purse string sutures, bring the device ends together, and perform the anastomosis.

As mentioned, to use some of the devices above, each portion of the colon or other vessel to be reconnected is usually provided with a purse-string suture. Purse string sutures are continuous, circular inverting sutures, used to close a tubular section of tissue, e.g., intestinal tissue, prior to the performance of the end-to-end anastomosis with a suturing instrument. As such, a purse string suture is a single thread stitched to surround an opening of the tubular section and then is pulled tight (like a purse-string) to close the hole.

Typically, a purse string suture is attached to a surgical needle that is used by a surgeon to manually stitch the purse string suture about the periphery of the tubular section of tissue. A purse string suture is a suture loosely placed around cut end of a vessel (e.g., any end of an intestinal organ) in a manner to act as a purse string so that after the purse string suture is stitched to the tissue, the ends of the purse string suture can be pulled to tighten the stitches and draw the tissue together (e.g., like closing a purse). Then, the purse string suture is wrapped and tightened about the tubular section of tissue. In the manual stitching of the purse string suture, it can be difficult to obtain uniform penetration of the purse string suture into the tissue. It also can be difficult to obtain stitches that are uniform in length and are evenly spaced apart. As a result, some of the stitches may rip away from the tissue when the ends of the purse string suture are pulled. Further, at times, it may be difficult for the surgeon to reach an area within the human body cavity to place the purse-string suture.

Another drawback of applying purse string sutures manually is that a surgical opening large enough to fit the surgeon's hands may be required. With the progression toward less invasive surgical techniques, e.g., laparoscopic surgery, that permit visualization and manipulation of surgical instruments through less invasive openings in the human body, a compact surgical instrument is desired that automatically places purse string sutures in tissue structures and obviates the need for space to view the stitching procedure and accommodate the surgeon's hands.

Accordingly, a surgeon may alternatively use a purse string device to apply the suture. Purse string suture devices are known that comprise a pair of serrated tissue clamping jaws provided with teeth for clamping the tissue to be sutured therebetween. Such devices include needle passages which extend through the teeth on each jaw for receiving a needle attached to a suture to be threaded through the tissue. In use, the tissue to be sutured is clamped between the jaws and the needle is manually passed through the needle passages in both jaws to thread the suture through the tissue. Thereafter, the jaws are opened and the purse string suture is tightened and wrapped to draw the tissue together. Many variations of this device that use a clamping mechanism are known, so as to clamp the end of a vessel tube and apply the suture to close the opening.

In use it is desired that a sufficient amount of tissue be clamped and pinched into the spaces between the clamping jaws to receive the needles and suture threads that are driven through the passages in the jaws. However, due to configurations of the jaws and spaces therebetween, at times only a limited amount of tissue may be pinched into the path of the needles. Thus, it is possible that an insufficient amount of tissue may be gathered into the spaces between the teeth to properly perform the purse string suturing technique.

Another obstacle is the size of the device. It is not always possible to use such devices in the desired place within the human body cavity due to size of the device and lack of maneuverability of the surgeon within the cavity. For example, it is not always desirable to create an opening in the human body large enough to place the clamp-like purse string suture device in position to apply the suture. As such, depending on the location of the vessel, size of the vessel, etc., it is often difficult, if not virtually impossible, to place a suitable purse string suture in a manner so as to insure a desirable reconnection of the vessel. This is true, for example, in low colon anastomosis where it may be difficult to place the purse string suture on a distal end of the vessel especially using less invasive laparoscopic purse-string suturing techniques.

SUMMARY

Within the present application presented below, a surgical instrument is provided for applying purse string sutures to tissue. The surgical instrument includes a first and second purse string plate, and a first and second push plate. The first purse string plate has notches for receiving tissue and through which a first suture wire may pass. The first push plate advances a first suture wire through the notches of the first purse string plate and into the tissue to enable application of a first purse-string suture. The second purse string plate also has notches for receiving tissue and through which a second suture wire may pass, and the second push plate advances a second suture wire through the notches of the second purse string plate and into the tissue to enable application of a second purse-string suture. The first and second purse-string sutures may be applied by pulling the suture wires through the tissues to thread sutures that may be attached to the suture wires through the tissue as well. Subsequently, the sutures can be tightened to close an opening of the tissue.

In another embodiment, the surgical instrument may include a purse string plate, a shaft and a push plate. The purse string plate has notches or slots formed in a perimeter or outer surface boundary of the circular disc between flanges that receive tissue and through which a suture wire may pass. Each flange includes a passage through which the suture wire may pass. The shaft may apply suction to the purse string plate to draw portions of the tissue into the notches of the purse string plate, and the push plate can advance the suture wire through the notches of the purse string plate and into the tissue. In this manner, the suture wire may be threaded into a perimeter of a vessel wall, and can be used to thread a suture through the vessel wall. The suture can be pulled tight to close the vessel and create a purse string suture.

In still another embodiment, the surgical instrument may include two purse string plates, push plates, suture and a shaft. The two purse string plates are connected by a disc connector positioned between the two purse string plates. Each purse string plate has notches or openings in a perimeter of the purse string plate for receiving tissue and through which a suture wire may pass. The push plates may advance respective suture wires through the notches of the two purse string plates and into a first and second portion of the tissue. Buckle bridges may be present along the length of the shaft of the device to hold the suture wire in place while advancing the suture wire through the notches of the purse string plate. Suture is within the first push plate and connected to an end of the suture wire that will pass through one of the purse string plates. Suture is also within the second push plate and connected to an end of the suture wire that will pass through the other one of the purse string plates. The shaft may apply suction to the purse string plates to draw the tissue into the respective notches of the purse string plates so that the respective suture wires may pass through the tissue. Subsequently, the suture wires may be pulled through the tissue to pull the sutures attached to the suture wires through the tissue and create two purse-string sutures.

The surgical instrument of the present application may be used to automatically apply multiple purse string sutures from within a vessel to close an opening at an end of a tubular vessel. Being able to apply the suture from inside of a vessel allows for less invasive surgical techniques to be used in instances of colorectal surgery, for example. Further, having the ability to apply multiple purse string sutures facilitates performing an end-to-end anastomosis procedure of the lower colon using laparoscopic procedures.

These as well as other aspects and advantages will become apparent to those of ordinary skill in the art by reading the following detailed description, with reference where appropriate to the accompanying drawings. Further, it is understood that this summary is merely an example and is not intended to limit the scope of the invention as claimed.

BRIEF DESCRIPTION OF THE DRAWINGS

FIGS. 4A and 4B illustrate examples of a specimen suture disc and a distal suture disc of the medical device of FIG. 1.

FIG. 5 illustrates an example of a suture connected to two suture wires.

FIG. 7 is an example conceptual illustration of operation of the medical device shown in FIG. 1.

FIG. 8 is an example conceptual illustration of applying a purse string suture.

DETAILED DESCRIPTION

Within embodiments described below, a medical device is provided for applying purse string sutures to an internal wall of a vessel to facilitate anastomosis of the vessel. The device may be used, for example, to apply two purse string sutures to the colon by inserting the device into the anus and applying the purse string sutures internally to the colon. In this manner, the purse string sutures may be set prior to excising a portion of the colon. By applying the purse string sutures through a naturally occurring opening in the human body, e.g., the anus, a less invasive medical procedure is possible.

The medical device presented herein may apply one or more purse string sutures to any vessel or hollow tube-like tissue, such as to an intestinal tissue or intestinal vessel (e.g., colon).

Figure 1:
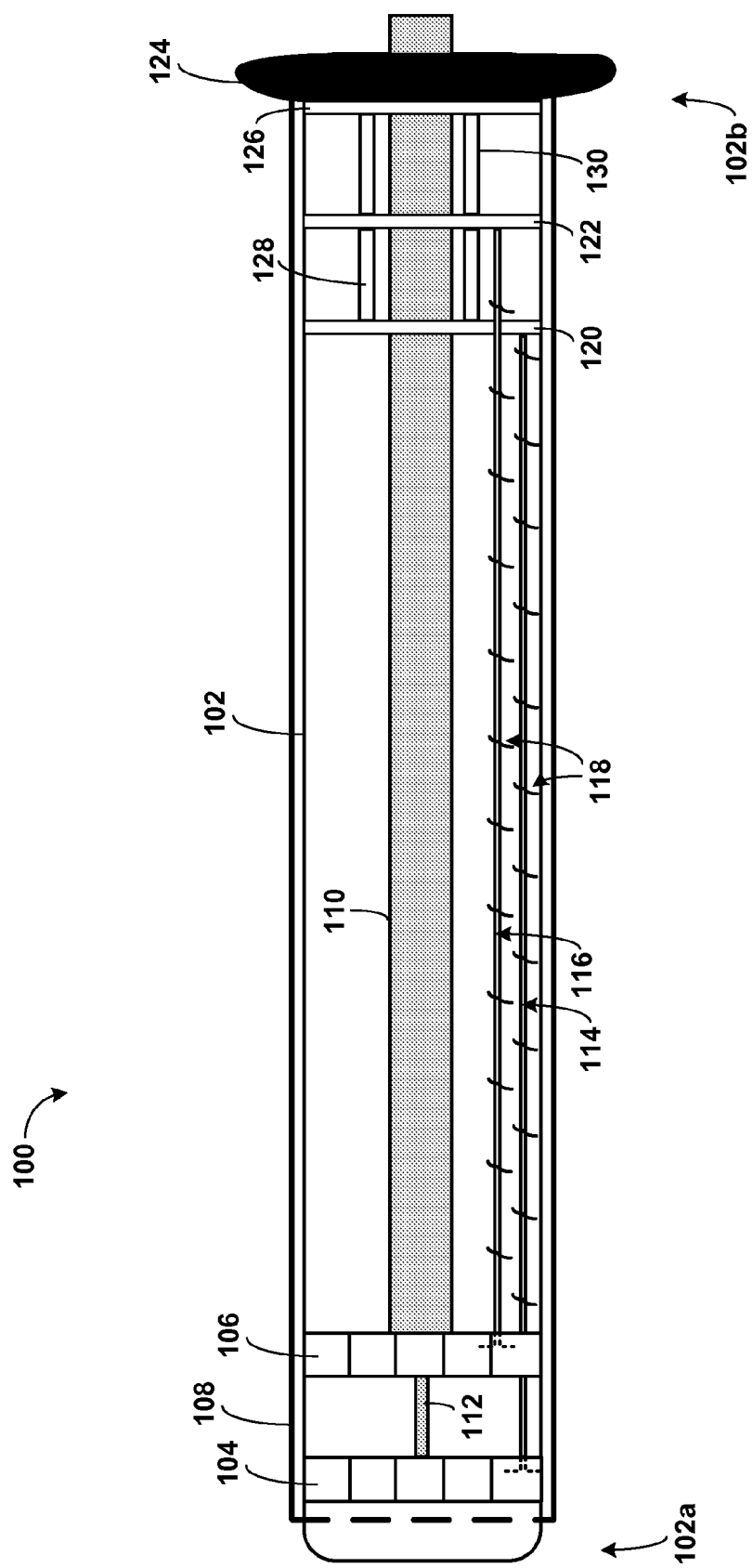
FIG. 1 is an example illustration of a medical device for applying purse string sutures.

FIG. 1 is an example illustration of a medical device 100 for applying purse string sutures. The device 100 includes a housing 102 with a front end 102a and a back end 102b. Two purse string plates 104 and 106 are located at the front end 102a of the housing 102, and a plate protector 108 surrounds the housing 102 including surrounding the two purse string plates 104 and 106 (or referred to jointly as a plate unit). The purse string plates 104 and 106 may be circular in shape and may have, for example, a 33 mm diameter (103.62 mm circumference) or a 29 mm diameter (91.06 mm circumference). Other sizes and shapes are also possible and may be used depending on a size of the vessel to which the medical device 100 will be inserted. For example, the plates may be substantially circular or have an elliptical or oval shape as well.

A center guide post or shaft 110 extends from the purse string plate 106 to the back end 102b of the housing 102. The center guide post 110 is connected to the purse string plate 104 through a connector 112. Suction may be applied through the center guide post 110 to the purse string plates 104 and 106.

Two suture wires 114 and two suture wires 116 are within the housing 102 and held in place by buckle bridges 118. The suture wires 114 extend between purse string plate 104 and a specimen suture plate 120, while the suture wires 116 extend between the purse string plate 106 and a distal suture plate 122. The suture wires 114 and 116 are advanced through openings within perimeters or outer surfaces of the purse string plate 104 and 106 by the specimen suture plate 120 and the distal suture plate 122. A turn-knob 124, for example, may be used to push a plate 126 that advances push rods 128 and 130, which contact the specimen suture plate 120. The rods 128 and 130 pass through the distal suture plate 122 and contact the specimen suture plate 120. The rods 128 and 130 will advance the specimen suture plate 120 forward, which in turn, advances the suture wires 114 into the purse string plate 104. Once the push plate 126 is advanced forward and contacts the distal suture plate 122, by further turning the turn-knob 124 the plate 126 will advance the distal suture plate 122 forward, which advances the suture wires 116 into the purse string plate 106.

Thus, the specimen suture plate 120 and the distal suture plate 122 push and advance the suture wires 114 and 116 forward, while the push plate 126 pushes and advances both the push rods 128 and 130 and the distal suture plate 122 forward. In alternative designs, only one push rod may be used to push the specimen suture plate 120.

The guide post 110 will rotate by turning the turn-knob 124 so that the push plate 126, which may be threaded, can advance along the guide post 110. Although a turn-knob 124 is described as advancing the push plate 126, other mechanisms are possible as well. For example, a plunger mechanism may be attached to the push plate 126 so that by pushing the plunger, the push plate 126 advances forward.

The suture wires 114 and 116 may have a length of about 110-120 mm so as to be able to traverse through an entire length of the perimeter of the purse string plates 104 and 106 (e.g., each disc may have a 33 mm diameter and a 103.62 mm circumference). It follows that the initial distance between the distal suture plate 122 and the purse string plate 106 is also about 110-120 mm to allow the suture wires 114 and 116 to be fully advanced through the purse string plate 106. Of course, the purse string plates 104 and 106 and the suture wires 114 and 116 may be any desired size and length depending upon the size of the vessel into which the purse string suture will be applied.

Figure 2:
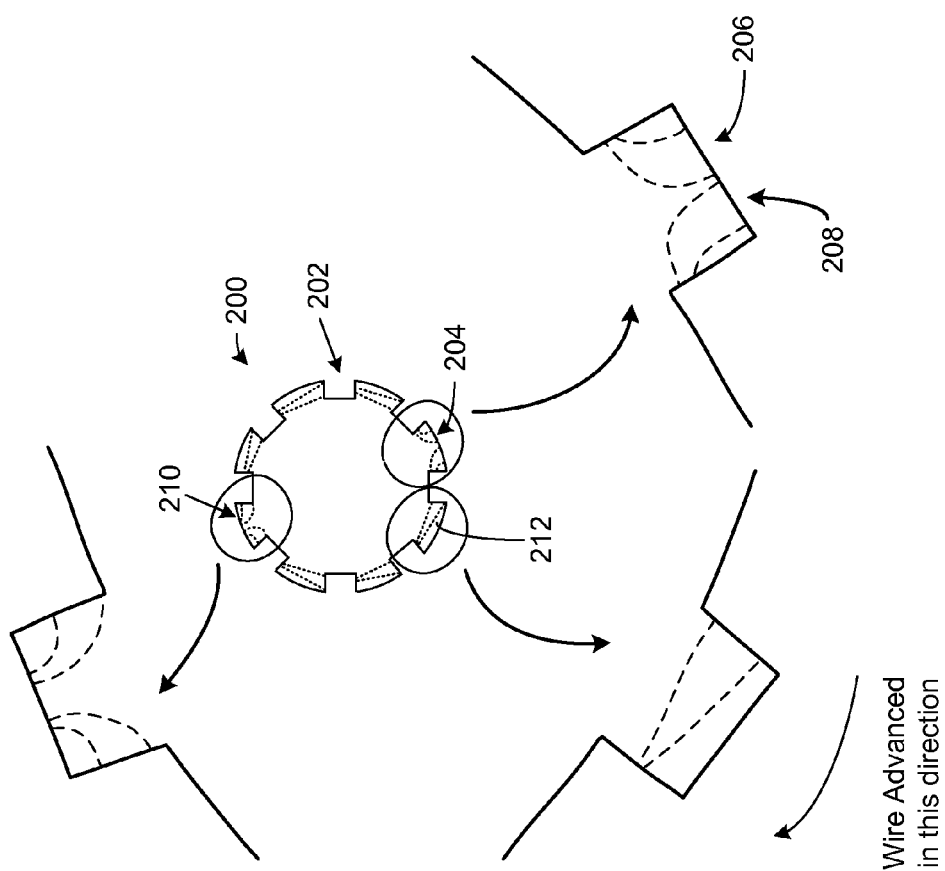
FIG. 2 is an example illustration of a purse string disc for the medical device of FIG. 1.

FIG. 2 is an example illustration of a purse string plate 200 (e.g., reference number 104 or 106 in FIG. 1). The purse string plate 200 may comprise plastic or other suitable materials. In the example shown in FIG. 2, the purse string plate 200 is a circular disc, however, the purse string plate 200 may be other shapes as well. The purse string plate 200 includes multiple slots, such as slot 202. The purse string plate 200 may include any number of slots depending on a desired number of stitchings to be placed into the tissue. The slots are openings within a perimeter of the purse string plate 200 to receive portions of the tissue. In turn, a suture wire, as described above, can be advanced through the slot and through the tissue within the slot. Between the slots are flanges or protrusions, such as flange 204.

One flange 204 within the plate 200 is designed to receive the suture wire and provide an opening to direct the suture wire outside of the plate 200. The flange 204 includes two tapered wire tunnels. One tunnel 206 is designed to receive one of the suture wires and another tunnel 208 is designed to receive the other suture wire 114. The tunnels 206 and 208 are tapered so as to provide a larger opening to receive the wire and a smaller opening to direct the suture wire outward. Another flange 210 is designed to direct the suture wires 114 outside of the purse string disc. In this manner, each of the suture wires 114 will traverse through half of the purse string disc. Each remaining flange, such as flange 212, includes a tapered tunnel to facilitate direction of the suture wire around the perimeter of the plate 200.

Figure 3A:
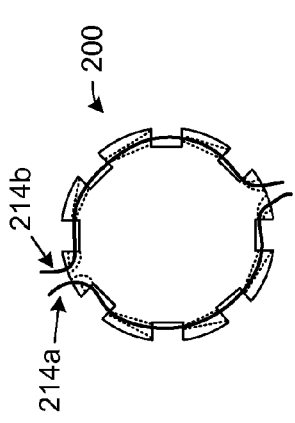
FIGS. 3A-3B are example conceptual illustrations of operation of the purse string disc of FIG. 2.
Figure 3B:
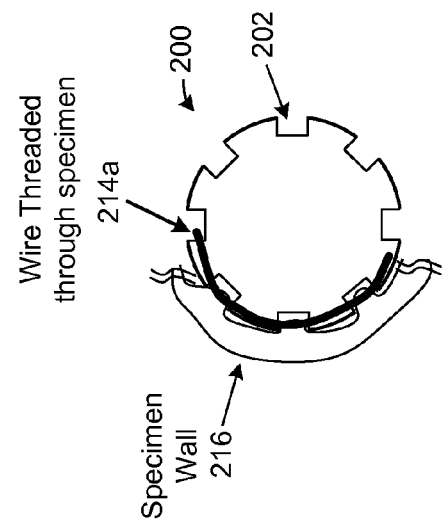

FIG. 3A illustrates two suture wires, wires 214*a-b*, advanced through the flanges of the plate 200. Each wire 214*a-b* traverses through half of the plate 200. The medical device 100 can be inserted into a vessel, and the slots of the plate 200 are designed to receive an internal portion of the vessel's tissue wall. This is illustrated in FIG. 3B. Portions of a specimen wall 216, e.g., internal wall of a colon, can be received into the slots using a suction means (described below). Following, the suture wire 214*a* can be advanced through the tunnels within each slot and through the portion of the specimen wall contained within each slot. Another suture (e.g., 214*b*) is advanced through the opposite half of the disc 200 as well (shown in FIG. 3A).

FIGS. 4A and 4B illustrate examples of a specimen suture plate 402 and a distal suture plate 414 of the medical device shown in FIG. 1. The specimen suture plate 402 is a 2-layer hollow plate and has a suture 404 preloaded within the plate 402. Each end of the suture 404 is connected to a separate suture wire within a window 412 in the front side of the specimen suture plate 402 within the medical device (e.g., in FIG. 1, a suture within the specimen suture disc 120 is connected to the suture wires 114). The suture 404 can be glued or crimped to the suture wire. FIG. 5 illustrates the ends of the suture 404 connected to suture wires.

The specimen suture plate 402 is advanced forward by push rods 128 and 130 in FIG. 1, and in turn, the specimen suture plate 402 advances a suture wire into a purse string plate. The specimen suture plate 402 includes an opening 408 for the suture wire connected to the distal suture plate 414 so that when the specimen suture plate 402 is advanced forward, the suture wire connected to the distal suture plate 414 remains in place. Similarly, the specimen suture plate 402 includes an opening 410 for the center guide post as well. In addition, the specimen suture plate 402 includes a knife 406 to cut the buckle bridges holding the suture wire in place as the specimen suture disc 402 is advanced forward. The buckle bridges may be plastic or other material that can be cut and set aside as the specimen suture plate 402 advances forward.

Similar to the specimen suture plate 402, the distal suture plate 414 has a suture 416 preloaded within the plate 414. The suture is connected to a suture wire at 418 within the medical device (e.g., in FIG. 1, a suture within the distal suture plate 122 is connected to the suture wires 116). The distal suture plate 414 is advanced forward by a push plate (e.g., plate 126 in FIG. 1), and in turn, the distal suture plate 414 advances a suture wire into a purse string plate. The distal suture plate 414 includes an opening 410 for the center guide post and two openings 420 and 422 for the push rods 128 and 130. In addition, the distal suture plate 414 includes a knife 424 to cut the buckle bridges holding the suture wire in place as the distal suture plate 414 is advanced forward.

Figure 6A:
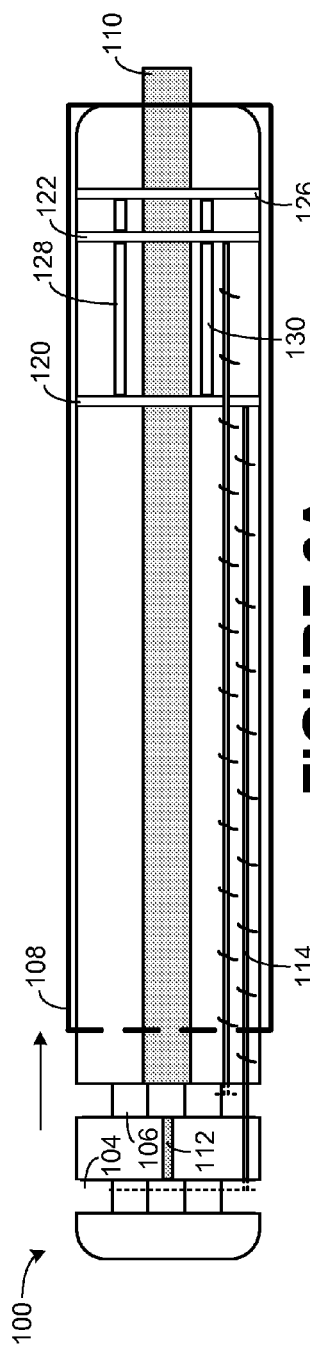
FIGS. 6A-6C illustrate an example operation of the medical device shown in FIG. 1.
Figure 6B:
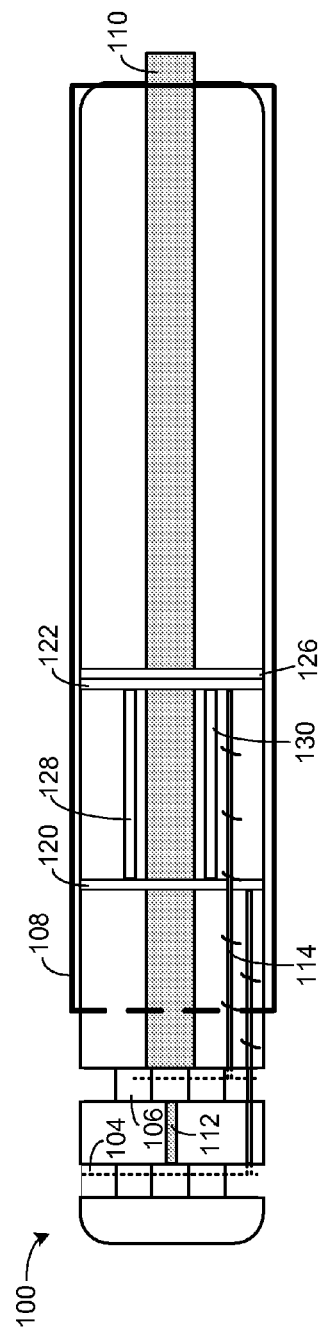
Figure 6C:
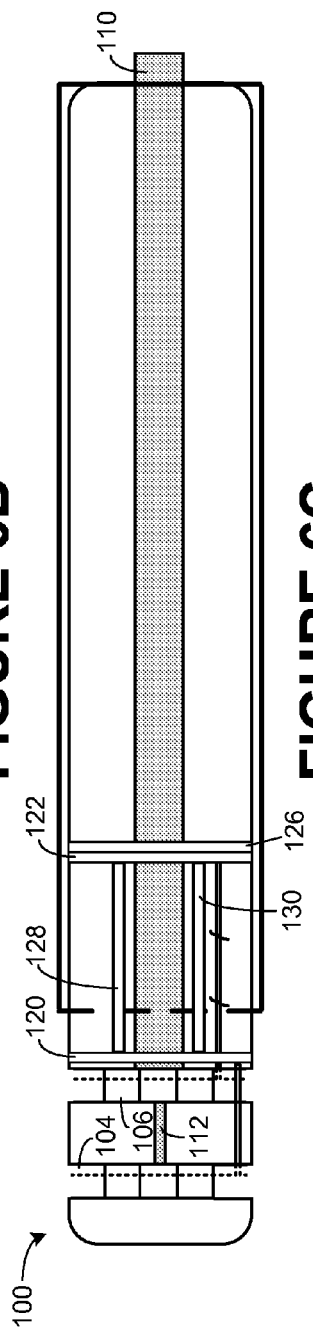

FIGS. 6A-6C illustrate an example operation of the medical device, as shown in FIG. 1. Initially, the medical device 100 is placed within the vessel. For example, the device 100 can be inserted into the colon through the anus. Following, suction is activated through the center guide post 110. In doing so, suction is applied to the slots of the purse string plate 104 and 106. As shown in FIG. 6A, the disc protector 108 is then partially retracted so as to expose the purse string plate 104 and 106. The plate protector 108 may include a spring mechanism, so that the disc protector can be manually retracted. Alternatively, the plate protector 108 could simply be held in place by the surgeon, and once a suture is to be placed, the surgeon may slide the plate protector 108 away from the front end of the device 100. As another example, the plate protector 108 may screw downward from a housing of the medical device 100. Still further, the plate protector 108 may snap into two positions; a first position to cover the purse string discs, and a second position to expose the purse string discs to a specimen wall.

Suction will be applied through the guide post 110 and draw a tissue wall of the specimen into the open slots of the purse string plate 104 and 106. As shown, openings are present within portions of the housing so as to enable the specimen to be received into the slots of the purse string plate 104 and 106. Suction may be applied through the center guide post 110 and the purse string plate connector 112 simultaneously to both purse string plate 104 and 106. Suction is applied to the vessel wall, however, only when the plate protector 108 is retracted. Suction is deactivated when the purse string plate connector 112 is snapped, opening suction to the peritoneal cavity (described below). The plate protector 108 is provided to allow a smooth surface to pass along the vessel wall when inserting the device 100, rather than inserting the device 100 into the vessel and exposing the notches/slots of the purse string plate 104 and 106 to the entire vessel wall.

The turn-knob 124 can be rotated to advance the push plate 126 so as to advance the specimen suture plate 120. The push rods 128 and 130 will pass through the distal suture plate 122 so as to only advance the specimen suture plate 120, which in turn, advances the two suture wires 114. Ball bearings or other mechanisms can be used to facilitate advancement of the suture disc 120. The buckle bridges 118 keep the suture wires 114 from bending while advancing, and the knife on the specimen suture plate 120 breaks the buckle bridges as the specimen suture plate 120 advances. The suture wires 114 advance through the specimen that has been received into the slots of the purse string plate 104 using suction. The suture wire 114 will advance out of the purse string plate 104 through a side of the plate 104 and be visible on an anterior external vessel wall. Each end of the suture wires 114 can be grasped with a laparoscopic grasper and pulled out through a cannula. A suture is attached to the other ends of the suture wires 114, so that by pulling the two ends of the suture wires out of the purse string plate 104, the suture is placed into the specimen. The wires can be cut off and an extracorporeal knot is then tied to close an opening of the specimen.

The advancement of the plate 126 initially advanced only the specimen suture plate 120 by advancing the push rods 128 and 130 through the openings 420 in the distal suture plate 122. Once the plate 126 contacts the distal suture disc 122, the distal suture plate 122 is advanced simultaneously with the specimen suture plate 120. This is shown in FIG. 6B. The distal suture plate 122 will, in turn, advance the suture wires 116. The buckle bridges 118 keep the suture wires 116 from bending while advancing, and the knife 422 on the distal suture plate 122 breaks the buckle bridges as the distal suture plate 122 advances. The suture wires 116 advance through the specimen that has been received into the slots of the purse string plate 106 using suction. The suture wires 116 will advance out of the purse string plate 106 through a side of the plate 106 and be visible on an anterior external vessel wall. The two ends of the suture wires 116 can be grasped with a laparoscopic grasper and pulled out through a cannula. A suture is attached to the two other ends of the suture wires 116, so that by pulling the suture wires out of the purse string plate 106, the suture is placed into the specimen. The wires can be cut off and an extracorporeal knot can later be tied to close the distal end of the vessel.

FIG. 6C illustrates both the specimen suture plate 120 and the distal suture plate 122 being fully advanced and the suture wires 114 and 116 being placed within the purse string plate 104 and 106 and the specimen.

Once the purse string suture wires have been pulled through/removed, two purse string sutures are placed in the specimen wall. To complete the medical procedure, the portion of the specimen to be removed, e.g., the rectum between the purse string plates, is cut using laparoscopic scissors. The purse string plate connector 112 is snapped by a laparoscopic grasper, separating the purse string plate 104 from the device 100. An example is shown in FIG. 7. On the proximal end of the device, the plate 104 acts as a cap to seal the opening of the specimen. The suture can be tied around the plate 104 to close the opening of the specimen for the time being.

At this point, suction is stopped, and withdrawal of the device 100 snaps the suture tunnels open that were held by suction allowing the distal purse string plate 106 to separate from the rectum wall. The flanges on the distal purse string plate 106 may be perforated or scored, so that by removing the device 100, the flanges break off the distal purse string plate 106 and allow the suture to remain in the distal end of the specimen. Alternatively, each flange on distal purse string plate 106 may include an opening on an underside of the flange so that when the device 100 is removed from the specimen, the suture may slide through the opening of the flanges and remain in the specimen. In this manner, the device 100 including the distal purse string plate 106 can be removed from the specimen without altering the suture that was placed in the distal end.

Once the device 100 is withdrawn, the distal end purse string sutures can be applied by pulling the suture wires 116 with a laparoscopic grasper and an extracorporeal knot can be tied to close the vessel, as shown in FIG. 8. The seal of the distal end may be less than that of the proximal end because the plate 104 is still present in the proximal end of the specimen to fully seal the opening. This is beneficial because the proximal end of the specimen will usually include contents, e.g., stool, and so it is important to ensure that no leakage occurs at the proximal end. In contrast, the distal end may include less or no contents, and thus providing a substantially sealed opening is sufficient.

The portion of the colon to be excised, including the portion with the plate 104, can now be extracted. In this manner, by placing the plate 104 in the portion to be extracted, the plate 104 is also removed with the excised portion. Thus, the portion of the colon to be excised is extracted, and an anvil is placed in the proximal bowel. An end-to-end anastomosis stapler cartridge can then be advanced to the purse string suture 116, and the suture 116 is tied around the center post of the stapler to perform the connection between the proximal and distal ends of the specimen.

Using the medical device of the present application can have many benefits and applications for laparoscopic surgery to remove portions of the colon, for example. The medical device allows for less invasive procedures to be taken, since the device is inserted through an existing orifice and fewer incisions are needed. Further, the device automates a procedure that can be difficult at times due to placement of the sutures within areas of the human body cavity that are not very accessible. Further, the device provides for a means to simultaneously divide the vessel and occlude the cut proximal end to prevent leakage of the vessel's contents.

The medical device automatically applies purse string sutures in that the medical device eliminates the manual application of sutures to the tissue by a surgeon, and quickly and accurately applies a suture to tissue with minimal steps and typically in less time than manual suturing.

In an alternate design, the medical device 100 may only include one purse string plate so that only one purse string suture is applied. In some medical procedures, only one purse string suture is desired, and to be able to apply the suture internally within a vessel can lower a difficulty of the procedure. Still, in other designs, the medical device 100 may include multiple purse string plates, however, only one suture may be applied. Other examples are possible as well.

It should be understood that the illustrated embodiments are examples only and should not be taken as limiting the scope of the present invention. The claims should not be read as limited to the described order or elements unless stated to that effect. Therefore, all embodiments that come within the scope and spirit of the following claims and equivalents thereto are claimed as the invention.

What is claimed is:

1. A surgical instrument for applying purse string sutures to tissue, comprising:
    a first purse string plate having notches for receiving tissue and through which a first suture wire may pass;
    a first push plate for advancing the first suture wire through the notches of the first purse string plate and into the tissue to enable application of a first purse-string suture;
    a second purse string plate having notches for receiving tissue and through which a second suture wire may pass;

a second push plate for advancing the second suture wire through the notches of the second purse string plate and into the tissue to enable application of a second purse-string suture; and a housing to house the surgical instrument, wherein the housing has a front end and a back end, and wherein the first purse string plate and the second purse string plate are within the front end of the housing, and wherein the housing is configured to be inserted into a human body.

2. The surgical instrument of claim 1, further comprising a guide post through which suction is applied to the first purse string plate and the second purse string plate to draw the tissue into the notches of the first purse string plate and the second purse string plate.

3. The surgical instrument of claim 2, further comprising a disc connector positioned between the first purse string plate and the second purse string plate and through which suction is applied to the second purse string plate.

4. The surgical instrument of claim 3, further comprising push rods to advance the first push plate.

5. The surgical instrument of claim 3, further comprising a disc protector surrounding the first purse string plate and the second purse string plate.

6. The surgical instrument of claim 5, wherein the guide applies suction to the first purse string plate and the second purse string plate to draw the tissue into the notches of the first purse string plate and the second purse string plate when the disc protector is retracted.

7. The surgical instrument of claim 1, further comprising a third push plate for advancing the second push plate.

8. The surgical instrument of claim 1, further comprising:
suture in the first push plate connected to an end of the first suture wire; and
suture in the second push plate connected to an end of the second suture wire.

9. The surgical instrument of claim 1, wherein the first suture wire is advanced through half of the notches of the first purse string plate, and further comprising another suture wire advanced by the first push plate through the other half of the notches of the first purse string plate.

10. The surgical instrument of claim 1, wherein the first purse string plate is a circular disc.

11. A surgical instrument for applying purse string sutures to tissue, comprising:
a purse string plate having notches formed in a perimeter of the purse string plate between flanges, the notches for receiving tissue and through which a suture wire may pass, the flanges including a passage through which the suture wire may pass;
a shaft through which suction is applied to the purse string plate to draw the tissue into the notches of the purse string plate;
a push plate for advancing the suture wire through the notches of the purse string plate and into the tissue; and
a housing to house the surgical instrument, wherein the housing has a front end and a back end, and wherein the purse string plate is within the front end of the housing, and wherein the housing is configured to be inserted into a human body.

12. The surgical instrument of claim 11, wherein the passage within the flanges through which the suture wire may pass is a tapered passage having an end for receiving the suture wire with a larger diameter than an end for exiting the suture wire.

13. The surgical instrument of claim 11, wherein one of the flanges of the purse string plate includes an opening for directing the suture wire inside remaining flanges of the purse string plate, and wherein one of the flanges of the purse string plate includes an opening for directing the suture wire outside of the purse string plate.

14. The surgical instrument of claim 11, further comprising:
a second purse string plate having notches formed in a perimeter of the second purse string plate between flanges, the notches for receiving tissue and through which a second suture wire may pass, the flanges including a passage through which the second suture wire may pass; and
a second push rod for advancing the second suture wire through the notches of the second purse string plate and into a second portion of the tissue.

15. The surgical instrument of claim 14 further comprising a connector that connects the purse string plate and the second purse string plate to form a disc unit.

16. The surgical instrument of claim 15, further comprising a disc protector surrounding a perimeter of the disc unit, and wherein suction is applied through the shaft to the purse string plate when the disc protector is retracted.

17. The surgical instrument of claim 11, further comprising:
buckle bridges for holding the suture wire in place within the housing while advancing the suture wire through the notches of the purse string plate.

18. The surgical instrument of claim 10, further comprising suture in the push plate connected to an end of the suture wire.

19. A surgical instrument for applying purse string sutures to tissue, comprising:
two purse string plates connected by a disc connector between the two purse string plates, each of the purse string plates having notches for receiving tissue and through which a suture wire may pass;
a first and second push plate for advancing respective suture wires through the notches of the two purse string plates and into a first and second portion of the tissue;
suture in the first push plate connected to an end of the suture wire that will pass through one of the purse string plates, and in the second push plate connected to an end of the suture wire that will pass through the other one of the purse string plates; and
a shaft through which suction is applied to the purse string plates to draw the tissue into the respective notches of the purse string plates so that the respective suture wires may pass through the tissue and pull the sutures through the tissue to create two purse-string sutures.

20. The surgical instrument of claim 19, further comprising a disc protector surrounding a perimeter of the two purse string plates, and wherein suction is applied through the shaft to the purse string plates when the disc protector is retracted.

* * * * *